(12) United States Patent
Park

(10) Patent No.: US 10,588,641 B2
(45) Date of Patent: Mar. 17, 2020

(54) CHIP FREE HIGH SPEED BONE CUTTING SYSTEM

(71) Applicant: THINK SURGICAL, INC., Fremont, CA (US)

(72) Inventor: Brian Youngbae Park, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

(21) Appl. No.: 15/566,957

(22) PCT Filed: Apr. 21, 2016

(86) PCT No.: PCT/US2016/028691
§ 371 (c)(1),
(2) Date: Oct. 16, 2017

(87) PCT Pub. No.: WO2016/172370
PCT Pub. Date: Oct. 27, 2016

(65) Prior Publication Data
US 2018/0125507 A1   May 10, 2018

Related U.S. Application Data

(60) Provisional application No. 62/150,280, filed on Apr. 21, 2015.

(51) Int. Cl.
*A61B 17/16* (2006.01)
*A61B 17/32* (2006.01)
(Continued)

(52) U.S. Cl.
CPC .......... *A61B 17/1622* (2013.01); *A61B 17/32* (2013.01); *A61B 17/50* (2013.01);
(Continued)

(58) Field of Classification Search
CPC ............ A61B 17/1622; A61B 17/1626; A61B 17/1628; A61B 17/50; A61B 17/32; A61B 17/32002; A61B 17/1615; A61B 17/1633; A61B 17/1644; A61B 90/05; A61B 2217/007; A61B 2217/005; A61B 2017/320084; A61B 2017/22079; A61B 2017/32007; A61B 10/025; A61B 2090/061; A61B 34/30; A61B 34/35; A61B 34/00; A61B 34/20; A61B 34/32;
(Continued)

(56) References Cited

U.S. PATENT DOCUMENTS

2002/0145724 A1* 10/2002 Wursch ................. B23B 49/008
356/4.01
2004/0191897 A1 9/2004 Muschler
(Continued)

*Primary Examiner* — Kevin C Sirmons
*Assistant Examiner* — Alexandra Lalonde
(74) *Attorney, Agent, or Firm* — Blue Filament Law PLLC

(57) ABSTRACT

A debris clearing system is provided that includes a tool having a suctioning intake positioned on an axis of the tool. A controller actuates the suctioning intake along the length of the axis of the tool. The suctioning intake is actuated while the tool is being operated and proximal to a surgical site on a patient's anatomy. A method of use is also provided for suctioning debris from a surgical field during a procedure.

18 Claims, 4 Drawing Sheets

(51) Int. Cl.
*A61B 17/50* (2006.01)
*A61B 90/00* (2016.01)
*B23Q 11/00* (2006.01)
*A61B 34/20* (2016.01)
*A61B 17/00* (2006.01)

(52) U.S. Cl.
CPC .......... *A61B 90/05* (2016.02); *B23Q 11/0046* (2013.01); *A61B 2017/00022* (2013.01); *A61B 2034/2055* (2016.02); *A61B 2090/061* (2016.02); *A61B 2090/065* (2016.02); *A61B 2217/005* (2013.01)

(58) Field of Classification Search
CPC . A61B 34/10; A61B 17/15; A61B 2034/2065; A61B 2034/101; A61B 2034/102; A61B 2034/105; A61B 17/17; A61B 17/1728; A61B 17/1695; A61B 2217/002; A61B 2217/00; A61B 2017/00022; A61B 2034/107; A61B 2034/108; A61M 1/0058; G06F 19/3481; A61F 2002/4645; B23Q 11/0046
See application file for complete search history.

(56) References Cited

U.S. PATENT DOCUMENTS

| | | | |
|---|---|---|---|
| 2005/0165420 A1 | 7/2005 | Cha | |
| 2008/0281343 A1 | 11/2008 | Dewey et al. | |
| 2010/0298835 A1* | 11/2010 | Ralph | A61B 17/1635 606/80 |
| 2010/0312102 A1* | 12/2010 | Barnes | A61B 17/1615 600/424 |
| 2011/0245833 A1* | 10/2011 | Anderson | B23B 49/02 606/80 |
| 2013/0035690 A1* | 2/2013 | Mittelstadt | A61B 17/17 606/79 |
| 2013/0060278 A1* | 3/2013 | Bozung | A61B 17/32002 606/205 |
| 2013/0213683 A1* | 8/2013 | Brewster | B23Q 11/00 173/198 |
| 2014/0093320 A1 | 4/2014 | Sullivan | |
| 2015/0142031 A1* | 5/2015 | Faller | A61B 17/320068 606/169 |
| 2015/0142033 A1* | 5/2015 | Stulen | A61B 17/320068 606/169 |
| 2016/0120553 A1* | 5/2016 | Xie | A61B 17/162 606/80 |

* cited by examiner

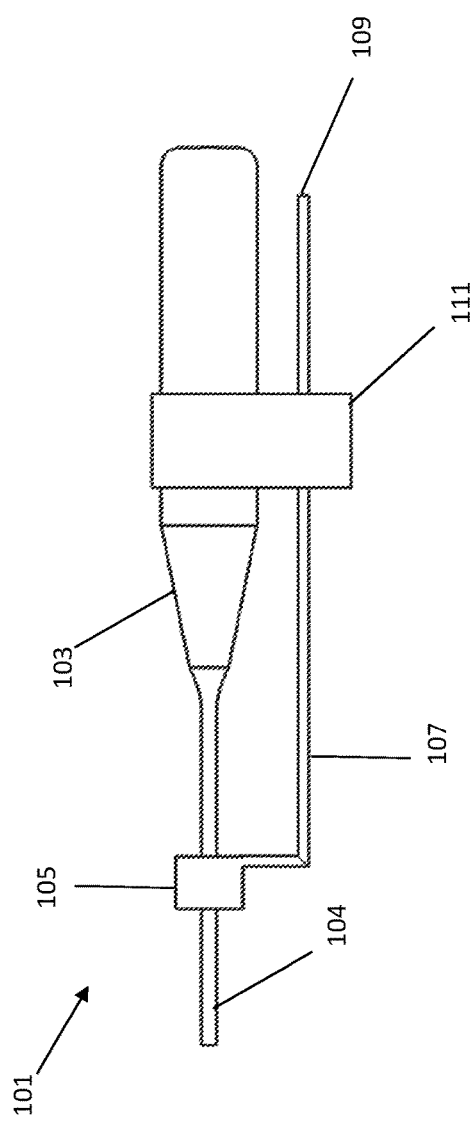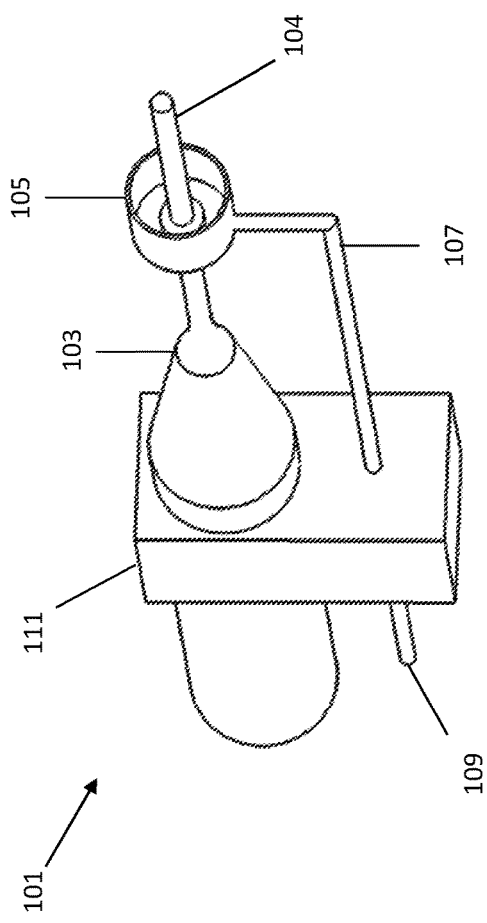

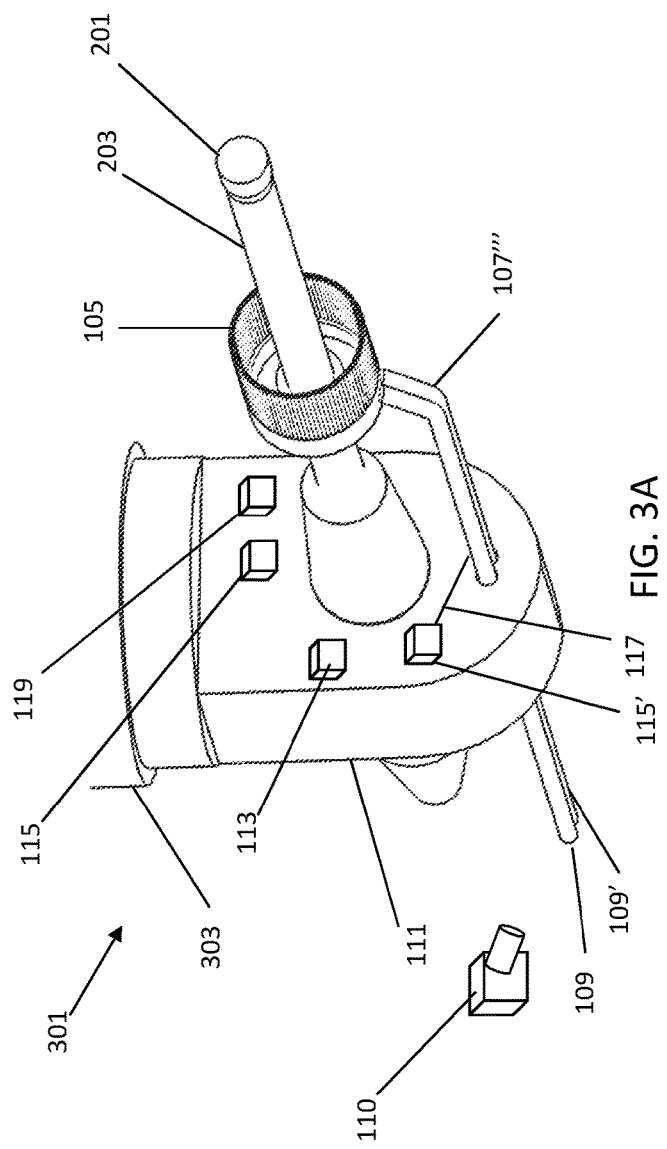
FIG. 3A
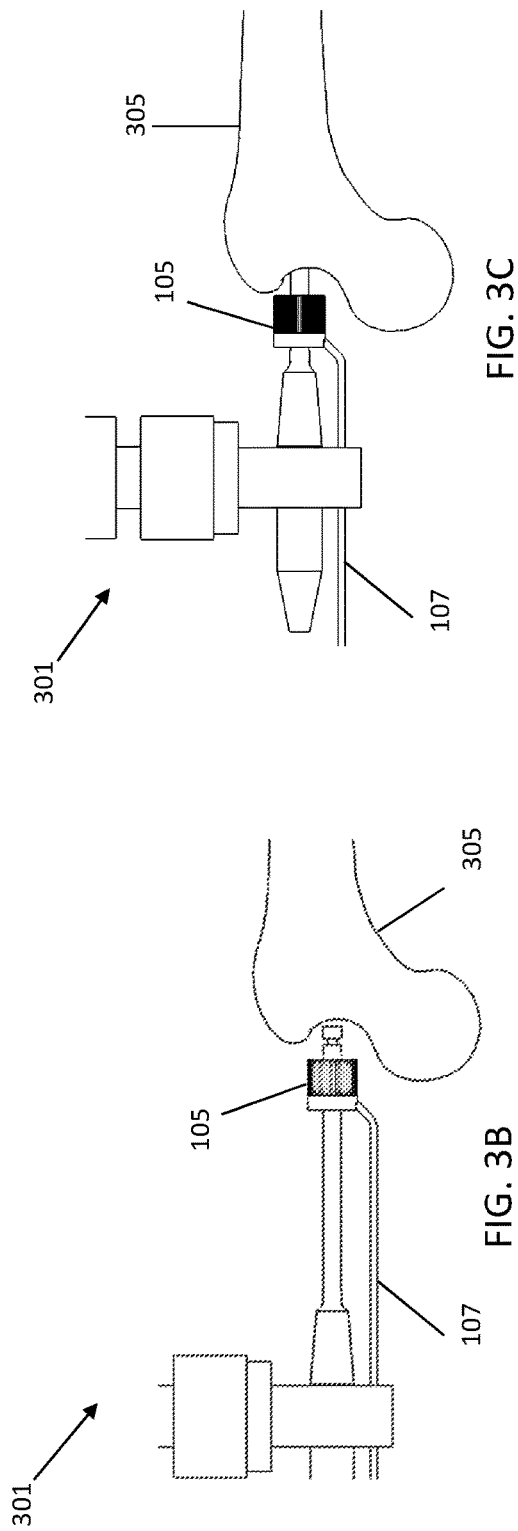
FIG. 3B
FIG. 3C

CHIP FREE HIGH SPEED BONE CUTTING SYSTEM

RELATED APPLICATIONS

This application claims priority benefit of U.S. Provisional Application Ser. No. 62/150,280 filed 21 Apr. 2015; the contents of which are hereby incorporated by reference.

FIELD OF THE INVENTION

The present invention generally relates to computer assisted surgery, and more specifically to a system and method for the irrigation and suction of debris during a surgical procedure.

BACKGROUND OF THE INVENTION

During a surgical procedure, fluids and other debris often fill the surgical site. The fluids and debris may obstruct the view of the targeted anatomy, as well as increase the risk of surgical site infection if not properly removed. Surgical site irrigation and cleaning are regularly performed during the surgical procedure to limit the aforementioned problems. In particular, joint arthroplasty is a surgical procedure to modify an arthritic, degenerated, or damaged joint with artificial components to improve the patient's quality of life and mobility. A joint replacement procedure is generally characterized by modifying the affected joint with a series of bone cuts to precisely receive artificial components, illustratively including plates, screws, knee implants, hip implants, and shoulder implants. During the bone modification, bone chips and bone debris are generated that need to be removed to reduce the risk of infection and improve post-operative healing.

Computer-assisted surgical systems have been developed to aid surgeons in creating the bone cuts to precisely receive the implant components. The high speed cutting instruments associated with the surgical systems may cause the bone debris to contaminate the operating area. When the depth of cutting is close to surface of the bone (where cortical bone is present or proximal), the risk of contamination is higher compared to cutting bone in a deeper cavity such as within the femoral canal. In addition, the bone debris generated during cutting may collide with the cutting tool and block the surgeon's view and thereby cause an interruption of the procedure. An accumulation of debris may also lead to a loss of accuracy in programmed cuts. Currently, various suction, irrigation, and wound cleansing devices are used to clear the fluids and other debris from a surgical site, and are usually manually controlled and operated by a medical assistant alongside the surgeon at the operating site. However, when an autonomous, semi-autonomous, or haptically controlled computer-assisted device is preparing the bone, it is often difficult to manually suction and irrigate the area due to the computer controlled movements of the system. Additionally, any suction or irrigation device placed on the cutting tool may inadvertently contact and damage surrounding soft tissue. The same holds true for any manually operated instrument such as an oscillating saw, surgical drill, and the like.

Thus there is a need in the art for a suctioning system that can efficiently clear debris in the operating site during a procedure that accounts for the operational movements of a surgical tool. There is a further need for a suctioning system that can be assembled directly to a surgical tool that accounts for any collisions with surrounding soft tissue.

SUMMARY OF THE INVENTION

A debris clearing system is provided that includes a tool having a suctioning intake positioned on an axis of the tool. A controller actuates the suctioning intake along the length of the axis of the tool. The suctioning intake is actuated while the tool is being operated and proximal to a surgical site on a patient's anatomy. A method of use is also provided for suctioning debris from a surgical field during a procedure.

BRIEF DESCRIPTION OF THE DRAWINGS

The present invention is further detailed with respect to the following drawings that are intended to show certain aspects of the present invention, but should not be construed as a limit on the practice of the present invention.

FIGS. 1A and 1B illustrate a side view and perspective view, respectively, of a suction surgical system in accordance with embodiments of the invention;

FIG. 3A illustrates a perspective view of a suction surgical system used with a robotic surgical system in accordance with embodiments of the invention;

FIGS. 3B and 3C illustrate the operation of a suction surgical system with a robotic surgical system in accordance with embodiments of the invention;

DETAILED DESCRIPTION OF THE INVENTION

Figure 2:
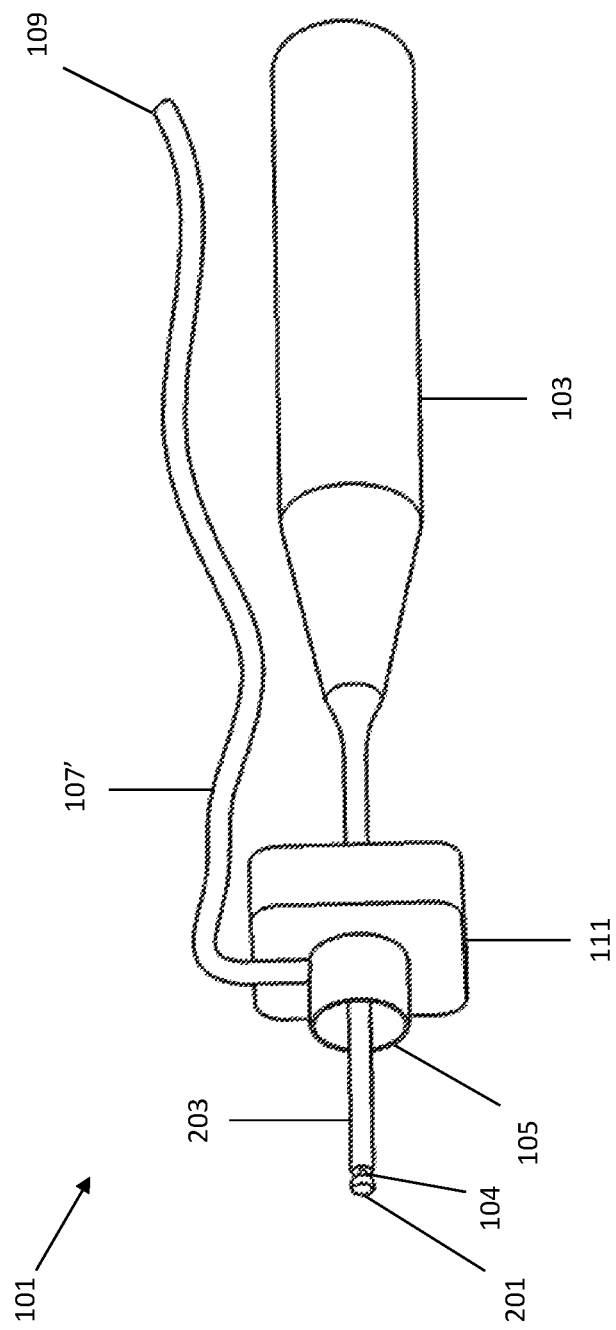
FIG. 2 illustrates a perspective view of an alternative configuration of the suction surgical system in accordance with embodiments of the invention.

The present invention has utility as a system to automatically aid in the clearing of debris created during a surgical procedure. The following description of various embodiments of the invention is not intended to limit the invention to these specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein, the term 'tool' may be any instrument capable of performing work on an external object. Tools illustratively include a probe, drill bit, cutter, burr, saw blade, shears, forceps, dissectors, cautery hook, cautery spatula, scissors, retractors, graspers; as well as any assembly used to house and/or operate the object contacting instrument.

The term, 'communication' is used to refer to the sending and/or receiving of data, current and/or energy either through a wireless or electrical connection.

As used herein, a fiducial marker may either be an active transmitter, such as an LED or electromagnetic emitter, or a passive reflector, such as a plastic sphere with a retro-reflective film. A fiducial marker array is an arrangement of two or more fiducial markers in a known geometric relationship in/on a rigid body of any geometric shape; an arrangement of three fiducial markers may be used to resolve all six degrees of freedom (6-DOF) of the rigid body.

Disclosed herein is the use of a tracking system. The tracking system includes at least one receiver to detect energy either emitted or reflected from a fiducial marker, and a tracking module with a processor coupled to the receiver to calculate a position and orientation (POSE) of a fiducial marker array to generate a tool position. The detectable energy may illustratively include, but is not limited to, optical, electromagnetic, infrared, ultraviolet, magnetic, fiber optic, acoustic, and targeted visible light. An example of an optical tracking system is the Polaris Spectra® Optical Tracking System (NDI Medical).

Also referenced herein are computer-assisted surgical systems which are to be considered synonymous with computer-aided surgical system, robotic surgical systems, navigation assisted surgical system, image-guided surgical systems and the like. Such systems illustratively include for example the NavioPFS™ Robotic Resurfacing System (Blue Belt Technologies), the RIO® Robotic System (Mako Surgical Corp.), the ROBODOC™ Surgical System (Think Surgical), the da Vinci® Surgical System, or any other computer-controlled device. It should also be appreciated that other non-computer controlled instruments and tools may be utilized by the subject matter disclosed herein including but not limited to power tools, drills, oscillating saws, inline power tools, screw-drivers, as well as any other tools. Additionally, various surgical applications are described below; however, it should be appreciated that other medical and non-medical applications can similarly exploit the subject matter disclosed herein.

Embodiments of the present invention describe a system capable of automatically clearing debris from a surgical site.

Referring now to the figures, FIGS. 1A and 1B depict a suction surgical system 101 in accordance with embodiments of the invention. The suction surgical system 101 includes a tool 103 with a rotating shaft 104, a suctioning intake 105 placed on the tool 103, and a controller 111 that actuates the suctioning intake 105 along the length of tool 103. The suctioning intake 105 may further include an elongate member 107 attached thereto. The suctioning intake 105 is actuated by the controller 111 while the tool 103 is being operated (manually or robotically) such that the suctioning intake 105 may remain as close as possible to the patient's anatomy without damaging the surrounding tissues. Therefore, debris and fluids may be safely and effectively removed from the surgical site automatically.

The controller 111 may include a microprocessor and a storage medium such as random access memory (RAM), read-only memory (ROM), flash memory or any other type of storage medium. The controller 111 in some inventive embodiments includes various external components to control the actuation of the suctioning intake 105. The external components may illustratively include gears, worm gears, screws, wheels and axels, cams, actuators, motors, step motors, micro-motors, servo-motors, encoders or various sensors. The various sensors may illustratively include contact sensors, force sensors, proximity sensors, distance measurement sensors, acoustic sensors, electric sensors, position sensors, pressure sensors, or any combination thereof.

In specific inventive embodiments, the controller 111 may actuate the suctioning intake 105 by interacting with an elongate member 107. The elongate member 107 may be actuated by the controller's 111 external components. For example, the elongate member 107 may include threads on the outer surface of the elongate member 107 to interact with a set of gears or screws in the controller 111. In a specific embodiment of the invention, with respect to FIG. 2, the controller 111 may be attached to or be a unitary structure with the suctioning intake 105. A sleeve 203 may envelope the rotating shaft 104 to provide support along the length of the tool 104. Bearings positioned within the sleeve 203 interact with the tool 104 such that the tool 104 may freely rotate within the sleeve 203. Like the elongate member 107', the controller 111 may actuate the suctioning intake 105 along the sleeve 203. The sleeve 203 may likewise have threads or other mechanisms positioned on the outer surface of the sleeve 203 that interact with the external components of the controller 111 to linearly actuate the suctioning intake 105 along the length of the sleeve 203. One of ordinary skill in the art will recognize a multitude of mechanisms to linearly actuate the suctioning intake 105.

In a particular inventive embodiment, the elongate member 107" may be or incorporate one or more hollow tubes (109, 109'), as shown in FIG. 3A. A distal end of the hollow tube(s) (109, 109') may be incorporated with and/or attached to the suctioning intake 105 to create a port between the suctioning intake 105 and a proximal end 109 of the hollow tube(s). The proximal end of the hollow tube(s) 109 or 109' may have a connection mechanism to attach various external devices 110. For example, the proximal end of hollow tube 109 may be connected to an external device 110 to create a pressure drop for removing debris at the suctioning intake 105. The external device 110 may illustratively include a vacuum, a pump, or any other surgical suction device. The elongate member 107''' may include a second hollow rigid tube 109'. The proximal end of the second hollow rigid tube 109' may be connected to an external device 110 that is a fluid pump. The fluid pump may direct fluids to irrigate, clean and/or aid in removing debris at the surgical site. The fluid may illustratively be water, saline, therapeutic agents, sanitization agents, gas, or combinations thereof. In some embodiments, the fluid is exposed to ultrasonic vibrations to better dislodge debris. In a specific embodiment, the fluid pump 110 may pulsate the fluid to assist in dislodging the debris. In a specific embodiment the external device 110 may be configured with an ultrasonic transducer to agitate and add bubbles to the injected fluid at the wound or surgical site to enhance the debris removal process. In an embodiment the pump 110 may have a fluid output port and a suctioning input port for collecting the injected fluid with collected debris.

The suctioning intake 105 may be actuated in response to various mechanisms. In specific inventive embodiments, the controller 111 and/or suctioning intake 105 may include a sensor 113 to detect if the suctioning intake 105 contacts any surrounding soft tissue. For example, a sensor 113 is a force and/or pressure sensor may be attached and/or incorporated with the controller 111 and/or the suctioning intake 105. If a force is detected above a given threshold the controller 111 may actuate the suctioning intake 105 away from the surgical site until the sensed force is below the threshold. Therefore the suctioning intake 105 may be positioned as near as possible to the patient's anatomy while protecting the surrounding soft tissue. The force and/or pressure threshold may be set such that the suctioning intake 105 is actuated away from the anatomy before causing serious injury to the tissue.

The controller 111 and/or the suctioning intake 105 may include a sensor 113 that is a proximity sensor to detect its relation to the surrounding tissue. The controller 111 may then actuate the suctioning intake 105 either towards or away from the tissue depending on a proximity range detected by the sensor. The proximity range may be set such that the suctioning intake 105 maintains an efficient and safe distance to the tissue to collect debris from the surgical site. In an embodiment, a distance measurement sensor may be included with the controller 111 and/or the suctioning intake 105. An electromagnetic signal may be pulsed by a transmitter and/or transceiver to the surrounding tissue and collected by a receiver and/or transceiver 115 to detect the distance between the suctioning intake 105 and the surrounding tissue.

In a specific inventive embodiment, displacement and/or distance measurement sensors may be utilized. For example, fiber optic cable(s) 117 may be embedded within and/or attached to the elongate member 107, the suctioning intake 105, the controller 111, or any combination thereof. A transmitter/receiver/transceiver 115' may be connected to one end of the fiber optic cable(s) 117. The transmitter portion of transmitter/receiver/transceiver 115' may send pulses of electromagnetic radiation through the fiber optic cable(s) 117 to be reflected off the patient's anatomy. The reflected signal is read by the receiver portion of transmitter/receiver/transceiver 115' and the distance between the suctioning intake 105 and the surrounding tissues may be calculated by a processor. The calculated distance may then be used by the controller 111 to actuate the suctioning intake 105 accordingly.

Similarly, a laser distance sensor 119 may be utilized. A transmitter, receiver and/or transceiver 115' may be attached to and/or incorporated with the suctioning intake 105, elongate member 107, controller 111, or any combination thereof. A laser beam from the laser distance sensor 119 may then detect the distance between the suctioning intake 105, the elongate member 107, or controller 111 from the surrounding tissue. The controller 111 may then actuate the suctioning member 105 accordingly to maintain a given distance to the tissues. Additionally, the spatial and geometric relationship between the suctioning intake 105, the elongate member 107, and the controller 111 may be known or calibrated prior to surgery. The controller 111 may further include a linear encoder to know the position of the suctioning intake 105 at any given time. A distance measurement sensor may be located on the suctioning intake 105, the elongate member 107, the controller 111, or any other external device that may also have a known spatial and geometric relationship relative to each other. If the distance measurement sensor is located, for example, on the controller 111, the distance of the suctioning intake 105 to the tissues will also be known due to the encoder values in the controller 111, and the known geometric and spatial relationships.

In a specific inventive embodiment, the sensor 113 (i.e. force sensor, distance measurement sensor, laser distance sensor, fiber optic sensor) may be programmed to allow a certain degree of contact between the suction intake 105 and the patient's anatomy. To improve debris removal and/or irrigation, it may be beneficial for the suctioning intake 105 to encapsulate the patient's anatomy but only to a degree that will not harm the tissue. For example, a force sensor may permit only a window of forces or a maximum force that the suctioning intake 105 may impose on the anatomy before retracting. A distance measurement sensor may allow a flexible portion of the suctioning intake 105 to contact the anatomy. If the distance between the suctioning intake 105 and anatomy are within a specified threshold, the suctioning intake 105 would then retract to a safe distance away or on the anatomy. Therefore, the suctioning system may improve the removal of debris and/or irrigation while still preserving the safety of the tissues.

In specific inventive embodiments, the controller 111 may be pre-programmed with operating instruction to actuate the suctioning intake 105 during a surgical procedure. In the case where the tool 103 is operated with pre-determined movements, the controller 111 may actuate the suctioning intake 105 accordingly. For example, a computer-assisted surgical system is illustratively shown in FIGS. 3A, 3B, and 3C. With respect to FIG. 3A, a tool 103 is attached to the distal link 303 of a computer-assisted surgical system 301. As illustratively depicted, the computer-assisted surgical system 301 assists a surgeon in preparing the femoral canal during total hip arthroplasty, where like numerals have the meaning ascribed thereto with respect to the previously mentioned figures. Prior to surgery, a pre-operative plan is created. The pre-operative plan may be created using software that allows the surgeon to virtually place an implant in a desired position and orientation on a three dimensional (3D) surface model of the patient's femur. The pre-operative plan is then transferred to the computer-assisted surgical system 301 in the operating room. The pre-operative plan may have a tool cut path that instructs various links and joints of the computer-assisted surgical system 301 to autonomously articulate the tool 103 to precisely create the cavity of the femoral canal according to the surgeon's plan. Likewise, the pre-operative plan may have instructions for the controller 111 to actuate the suctioning intake 105 with respect to the tool cut path. In other words, the pre-planned instructions for articulating the tool 103 and the pre-planned instructions for actuating the suctioning intake 105 coincide such that debris may be safely and effectively removed from the surgical site. For example, with respect to FIG. 3B, prior to cutting the surface of the femur 305, the suctioning intake 105 is actuated near a working portion of the tool 103 to collect debris at the femoral surface. As the tool 103 moves in and out of the femoral cavity during cutting, the controller 111 autonomously actuates the suctioning intake 105 according to the pre-operative plan illustratively shown between FIGS. 3B and 3C. It should be appreciated that the controller 111 may be a part of the hardware used to control the computer-assisted surgical system 301 (e.g. the controller 111 may be the same controller used to control a manipulator arm of the computer assisted surgical system 301)

Figure 4:
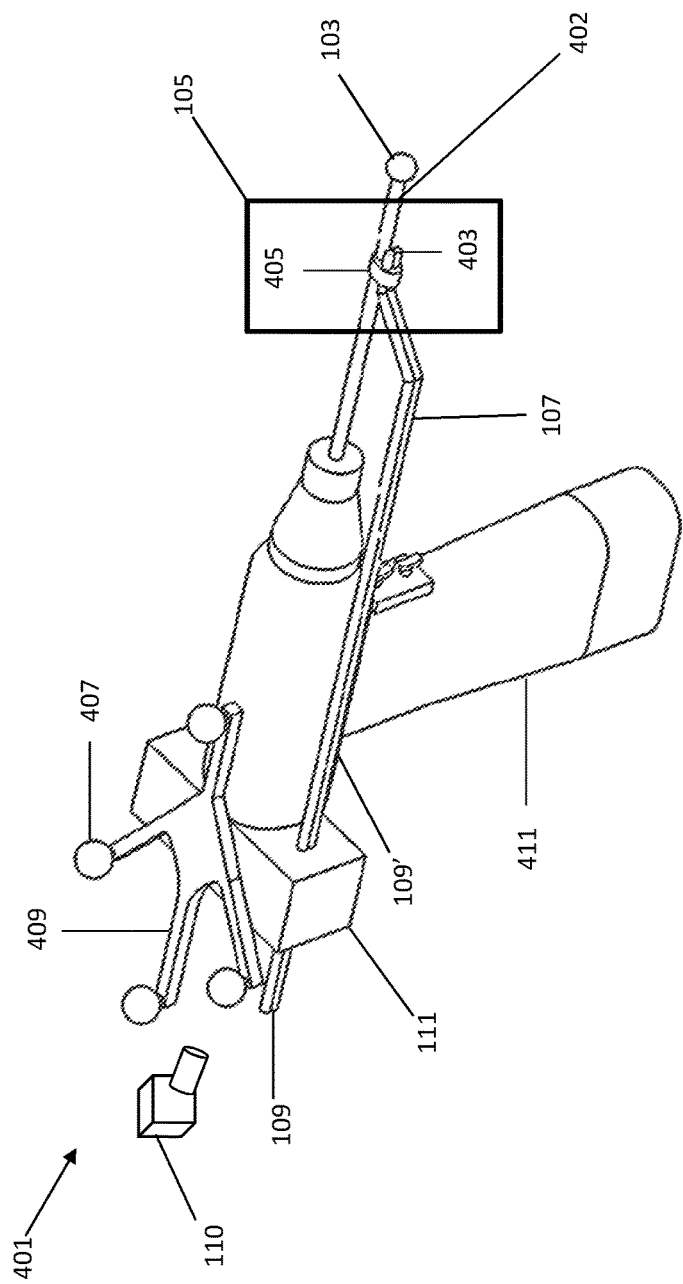
FIG. 4 illustrates a hand-held surgical tool with a suction surgical system in accordance with embodiments of the invention.

In a particular embodiment shown in FIG. 4, a hand-held surgical system 401 is provide, where like numerals have the meaning ascribed thereto in the previously mentioned figures. The hand-held surgical system 401 may include a handle 411, a working portion 402, and a fiducial marker array 409 with fiducial markers 407. The controller 111 may be incorporated and/or attached to the hand-held surgical system 401 at various locations, but preferably at a location that does not impede the user from operating the tool or visualizing the workpiece. The suctioning intake 105 may include one or more hollow tubes 403 attached to the tool 103 by an adapter 405. The controller 111 may be electrically or wirelessly connected to a tracking system that tracks the hand-held surgical system 401 by way of the tracking array 409. The tracking system may also track the anatomy or the workpiece. Prior to surgery, the suctioning intake 105, the controller 111, and the hand-held surgical system 401 may be calibrated and/or registered such that their spatial relationships are known relative to each other in 3D space. The controller 111 may further include an encoder to know the location of the suctioning intake 105 relative to the controller 111 during actuation. Then, during the operation, since the coordinates of the anatomy are tracked, the hand-held surgical system 401 is tracked and the spatial relationship between the hand-held surgical system 401, the controller 111 and the suctioning intake 105 are known, the controller 111 may accurately and precisely actuate the suctioning intake 105 without damaging the surrounding tissues.

In specific inventive embodiments, the suction surgical system 101 or 301 or 401 may have a plurality of operating modes. The actuation of the suctioning intake 105 may be done manually by a user in a manual mode, and controlled by the controller 111 in a control mode. This provides the user with a safety mechanism to override the controller 111 in case of a malfunction or a safety concern. Additionally, the manual mode may allow the user to re-position the suctioning intake 105 either closer or farther away from the surrounding tissues. For example, the user may need to get a better view of the patient's anatomy, and therefore manually translate the suctioning intake 105 away from the surgical site. Alternatively, the suctioning intake 105 may be in a surgical site that does not contain sensitive surrounding tissues, and therefore the user may manually translate the suctioning intake 105 onto the anatomy to irrigate and/or clear debris more effectively.

In a particular embodiment, the suctioning intake 105 may include an enclosure to trap debris within. As illustratively shown in FIGS. 1A, 1B, 2, 3A, 3B, and 3C the enclosure may have a wall with an inner void for trapping debris. The suctioning intake 105, the enclosure, and/or the walls may be made of a flexible material so as to reduce any injury that may occur in the event the enclosure contacts the patient's anatomy. In an embodiment, the walls may include a brush like structure with multiple fibers extending from the suctioning intake 105. The flexible material and/or brush will also reduce the chance of the tool 103 deflecting from a desired path if it contacts the patient's anatomy. It should be appreciated that the suctioning intake 105 may be designed in various configurations to remove debris from a surgical site. For example, in a particular embodiment, with respect to FIG. 4, the suctioning intake 105 may be the distal end of one or more hollow tubes 403 attached to the tool 103 by way of an adapter 405. The distal end of the one or more hollow tubes 403 may attach to the tool with an adapter 405 and are in fluid communication with proximal ends 109 and 109'. The proximal ends 109 and 109' are each independently, in some embodiments, in fluid communication with external devices 110. The adapter 405 may have a hollow tube(s) attachment member adjacent to a tool attachment member. The distal end of the hollow tube(s) 403 may slide into one portion of the adapter 405 and may be fastened thereto using a fastening element. Another portion of the adapter 405 may slide onto the tool 103 such that the distal end of the hollow tube(s) 403 may be actuated along the tool 103.

Figure 5:
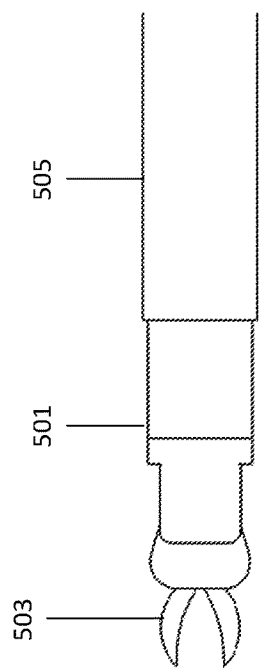
FIG. 5 illustrates a minimally invasive tool with a suction surgical system in accordance with embodiments of the invention.

In yet another embodiment, with respect to FIG. 5, the suctioning intake may be a hollow tube 505 that slides over a tool 501. The tool 501 may have a working portion 503 used in minimally invasive surgeries illustratively including laparoscopy. During a procedure, the hollow tube 505 may be actuated along the tool 501 until it passes over the working portion 503 of the tool 501 to clear debris from the surgical site.

In specific inventive embodiments, the suctioning intake 105 or 405, elongate member 107 or 107' or 107" and controller 111 are pre-assembled. For example, prior to surgery, a pre-assembly of these components, or a subset thereof is removed from a sterile package. The suctioning intake 105 or 405 may be placed about the tool 103 and the controller 111 attaches/latches and/or fits around another portion of the tool 103. The pre-assembly may be manufactured to fit specific tools. For example, the suctioning intake 105 or 405 may be manufactured with an inner diameter to fit the diameter of a specific tool. The elongate member 107 or 107' or 107" may be manufactured at a specific length corresponding to the length of the tool 103 or the surgery being performed. The controller 111 may be manufactured into various shapes and with different tool attachment capabilities. In a particular embodiment, the suctioning intake 105, elongate member 107 or 107' or 107" and controller 111 are manufactured with modifiable elements to assemble onto the tool 103. For example, the suctioning intake 105 or 405, controller 111 and/or elongate member 107 or 107' or 107" may have various fastening elements illustratively including screws, clamps, wires, or clasps that may aid in assembling each component to the tool 103. It should also be appreciated that the suctioning intake 105 or 405, controller 111, and/or elongate member 107 or 107' or 107" may be manufactured separately wherein the components are assembled prior to surgery in the operating room. It should further be appreciated that the suctioning surgical system 101 may be manufactured with any computer-assisted surgical system illustratively including the systems disclosed herein.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A debris clearing system for clearing of debris created during a surgical procedure at a surgical site on a patient's anatomy comprising:
   a tool connected to a robotic surgical system;
   a suctioning intake positioned on an axis of said tool;
   a pre-operative surgical plan residing on the robotic surgical system and having instructions for a controller to automatically adjust a position of said suctioning intake relative to the patient's anatomy as the controller automatically adjusts the position of said suctioning intake relative to a working portion of said tool; and
   said controller configured to actuate said suctioning intake along the axis of said tool while said tool is being operated to automatically clear the debris created during the surgical procedure.

2. The debris clearing system of claim 1 wherein said tool is at least one of a drill bit, cutter, burr, saw blade, shears, forceps, dissectors, cautery hook, cautery spatula, scissors, retractors, or graspers.

3. The debris clearing system of claim 1 wherein said controller further comprises a microprocessor, a storage medium, and a series of components to actuate and measure the movement and position of said suctioning intake.

4. The debris clearing system of claim 3 wherein said series of components further comprise one or more of gears, worm gears, screws, wheels and axles, cams, actuators, motors, step motors, micro-motors, servo-motors, encoders, a transmitter, a receiver, a transceiver, and sensors.

5. The debris clearing system of claim 4 further comprising an elongate member, said elongate member fixedly attached to said suctioning intake and movably connected to said controller for the actuation of said suctioning intake; and wherein said elongated member is configured to be actuated by at least one of said gears, worm gears, screws, wheels and axles, cams, actuators, motors, step motors, micro-motors, servo-motors, encoders.

6. The debris clearing system of claim 4 wherein said sensors further comprise at least one of contact sensors, force sensors, proximity sensors, distance measurement sensors, acoustic sensors, electric sensors, position sensors, pressure sensors, or any combination thereof.

7. The debris clearing system of claim 4 further comprising a fiber optic cable between said transceiver and said suctioning intake, where a series of pulses sent along said fiber optic cable generate a reflected signal from the surgical site used to determine a distance between said suctioning intake and the surgical site.

8. The debris clearing system of claim 1 further comprising one or more hollow tubes, where a distal end of said one or more hollow tubes is incorporated with or attached to said suctioning intake to create a port between said suctioning intake and a proximal end of said one or more hollow tubes; and wherein said proximal end of said one or more hollow tubes is configured for attachment to an external device.

9. The debris clearing system of claim 8 wherein said external device is a vacuum.

10. The debris clearing system of claim 8 wherein said external device is a fluid pump that directs one or more fluids to said suctioning intake.

11. The debris clearing system of claim 10 wherein said one or more fluids comprise water, saline, therapeutic agents, sanitization agents, gas, or combinations thereof.

12. The debris clearing system of claim 10 wherein said fluid pump further comprises an ultrasonic transducer.

13. The debris clearing system of claim 10 wherein said fluid pump further comprises a fluid output port and a suctioning input port for collecting an injected fluid with a series of collected debris from the surgical site.

14. The debris clearing system of claim 1 wherein said suctioning intake further comprises an enclosure, said enclosure having a wall with an inner void to trap debris.

15. The debris clearing system of claim 14 wherein said enclosure and said wall are made of a flexible material.

16. The debris clearing system of claim 14 wherein said wall further comprises a brush structure with a set of multiple fibers extending from said suctioning intake.

17. The debris clearing system of claim 1 wherein said suctioning intake is configured as a hollow tube that movably slides over said tool; and wherein during a procedure, the hollow tube is configured to be actuated along said tool until said hollow tube passes over the working portion of said tool to clear debris from the surgical site.

18. A method of using the debris clearing system of claim 1 comprising:

positioning said tool at the surgical site;

actuating said suctioning intake along said tool towards the surgical site; and wherein said suctioning intake is actuated while said tool is being operated.

* * * * *